US010517960B2

(12) United States Patent
Jakobsen et al.

(10) Patent No.: US 10,517,960 B2
(45) Date of Patent: *Dec. 31, 2019

(54) BIFUNCTIONAL POLYPEPTIDES

(71) Applicant: Immunocore Limited, Abingdon, Oxfordshire (GB)

(72) Inventors: Bent Karsten Jakobsen, Abingdon (GB); Annelise Brigitte Vuidepot, Abingdon (GB); Yi Li, Guangzhou (CN)

(73) Assignee: Immunocore Limited, Abingdon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/378,481

(22) Filed: Apr. 8, 2019

(65) Prior Publication Data
US 2019/0231895 A1 Aug. 1, 2019

Related U.S. Application Data

(63) Continuation of application No. 16/151,144, filed on Oct. 3, 2018, which is a continuation of application No. 13/319,597, filed as application No. PCT/GB2010/000988 on May 19, 2010, now Pat. No. 10,130,721.

(30) Foreign Application Priority Data

May 20, 2009 (GB) .................................. 0908613.3

(51) Int. Cl.
| A61K 47/68 | (2017.01) |
| C07K 14/725 | (2006.01) |
| A61K 47/64 | (2017.01) |
| C07K 16/46 | (2006.01) |
| C07K 16/28 | (2006.01) |
| A61K 38/00 | (2006.01) |

(52) U.S. Cl.
CPC ...... *A61K 47/6849* (2017.08); *A61K 47/6425* (2017.08); *C07K 14/7051* (2013.01); *C07K 16/2809* (2013.01); *C07K 16/46* (2013.01); *A61K 38/00* (2013.01); *C07K 2317/622* (2013.01); *C07K 2317/73* (2013.01); *C07K 2319/33* (2013.01)

(58) Field of Classification Search
None
See application file for complete search history.

(56) References Cited

U.S. PATENT DOCUMENTS

| 5,821,337 | A | 10/1998 | Carter et al. |
| 8,105,830 | B2 | 1/2012 | Weidanz et al. |
| 8,519,100 | B2 | 8/2013 | Jakobsen et al. |
| 9,068,178 | B2 | 6/2015 | Jakobsen et al. |
| 10,130,721 | B2 * | 11/2018 | Jakobsen ........... C07K 14/7051 |
| 2003/0223994 | A1 | 12/2003 | Hoogenboom et al. |
| 2004/0253632 | A1 | 12/2004 | Rhode et al. |
| 2006/0034850 | A1 | 2/2006 | Weidanz et al. |
| 2008/0044413 | A1 | 2/2008 | Hammond et al. |
| 2009/0042285 | A1 | 2/2009 | Weidanz et al. |

FOREIGN PATENT DOCUMENTS

| WO | WO 99/60120 A2 | 11/1999 |
| WO | WO 01/93913 A2 | 12/2001 |
| WO | WO 02/102299 A2 | 12/2002 |
| WO | WO 2003/020763 A2 | 3/2003 |
| WO | WO 2003/070752 A2 | 8/2003 |
| WO | WO 2004/033685 A1 | 4/2004 |
| WO | WO 2004/074322 A2 | 9/2004 |
| WO | WO 2005/113595 A2 | 12/2005 |
| WO | WO 2005/120166 A2 | 12/2005 |
| WO | WO 2006/037960 A2 | 4/2006 |
| WO | WO 2007/071426 A1 | 6/2007 |
| WO | WO 2008/135734 A1 | 11/2008 |
| WO | WO 2010/026377 A1 | 3/2010 |

OTHER PUBLICATIONS

Adams, Katherine, "Redirected T Cell Activity by High Affinity Tcr-Anti-CD3 Bispecific Candidate Therapeutics," Cardiff University for the Degree of Doctor of Philosophy, 2013, pp. 1-290.
Apr. 29, 2009 date stamped front page of the Journal of Immunotherapy, vol. 32, No. 4, obtained from the National Library of Medicine, 1 page.
Arnett et al., PNAS, vol. 101, No. 46, 2004, pp. 16268-16273, 2004.
Baeuerle et al., Current Opinion in Molecular Therapeutics, 2009, 11(1), 22-30.
Belmont, H., et al., "Potent antitumor activity of a tumor-specific soluble TCR/IL-2 fusion protein," Clinical Immunology, 2006, 121(1):29-39.
Bibollet-Ruche, F., et al., "The Quality of Chimpanzee T-Cell Activation and Simian Immunodeficiency Virus/Human Immunodeficiency Virus Susceptibility Achieved via Antibody-Mediated T-Cell Receptor/CD3 Stimulation Is a Function of the Anti-CD3 Antibody Isotype," Journal of Virology, Oct. 2008, pp. 10271-10278, vol. 82, No. 20.
Bluemel et al., Cancer Immunol Immunother (2010) 59:1197-1209.
Boulter et al. (Protein Engineering vol. 16 No. 9 pp. 707-711, 2003).
Bridgeman et al., Immunology, 135, 9-18 (2011).
Chames, P., et al., "Direct selection of a human antibody fragment directed against the tumor T-cell epitope HLA-A1-MAGE-A1 from a nonimmunized phage-Fab library," PNAS, Jul. 5, 2000, pp. 7969-7974, vol. 97, No. 14.
Choudhuri et al., Nature. Jul. 28, 2005;436(7050):578-82.
Davis et al., Nature Immunology, vol. 7., No. 8, 2006, pp. 803-809.
Denkberg, G., et al., "Selective Targeting of Melanoma and APCs Using a Recombinant Antibody with TCR-Like Specificity Directed Toward a Melanoma Differentiation Antigen," The Journal of Immunology, 2003, pp. 2197-2207, vol. 171.

(Continued)

Primary Examiner — Zachary S Skelding
(74) Attorney, Agent, or Firm — Fenwick & West LLP

(57) ABSTRACT

A bifunctional polypeptide comprising a specific binding partner for a peptide-MHC epitope, such as an antibody or T cell receptor, and an immune effector, such as an antibody or a cytokine, the immune effector part being linked to the N-terminus of the peptide-MHC binding part.

6 Claims, 9 Drawing Sheets

Specification includes a Sequence Listing.

(56) References Cited

OTHER PUBLICATIONS

Dissertation of Elisa Kieback, "A new safeguard eliminates T cell receptor gene-modified auto-reactive T cells after adoptive therapy," Oct. 23, 2008, 106 pages in total.
Dudley et al. (J Clin Oncol. Nov. 10, 2008;26(32):5233-9).
Hunder et al. (N Engl J Med. Jun. 19, 2008;358(25):2698-703).
International Search Report for PCT/GB2010/000988 dated Oct. 7, 2010.
Kirkwood et al., (J Clin Oncol. Jul. 10, 2008;26(20):3445-55).
Kjer-Nielsen et al. (PNAS 2004;101;7675-7680). (Year: 2004).
Li, B., et al., "Construction and characterization of a humanized anti-human CD3 monoclonal antibody 12F6 with effective immunoregulation functions," Immunology, 2005, pp. 487-498, vol. 116.
Lutterbuese et al. (J Immunother 2009;32:341-352).
MacCallum et al., J. Mol. Biol. (1996) 262, 732-745.
Marget, M., et al., "A HLA-Cw6 specific single-chain antibody fragment (scFv) recognizing a natural killer cell receptor epitope," Molecular Immunology, 2005, pp. 643-649, vol. 42.
Molhoj et al., Molecular Immunology 44 (2007) 1935-1943.
Molloy et al. (Current Opinion in Pharmacology 2005, 5:438-443).
Mosquera, L., et al., "In Vitro and In Vivo Characterization of a Novel Antibody-Like Single-Chain TCR Human IgG1 Fusion Protein," The Journal of Immunology, 2005, pp. 4381-4388.
Neethling, F., et al., "Assessing vaccine potency using TCRmimic Antibodies," Vaccine, 2008, 26(25):3092-102.
Offner et al., Molecular Immunology 43 (2006) 763-771.
Padlan et al., Molecular Immunology, vol. 31, No. 3, pp. 169-217, 1994.
Pan, S-H., et al., "Reduced Background Expression and Improved Plasmid Stability with pET Vectors in BL21 (DE3)," BioTechniques, Dec. 2000, pp. 1234-1238, vol. 29.
Richman et al. (Mol Immunol. Feb. 2009;46(5):902-16, Epub Oct. 29, 2008).
Rudolph et al. (Current Opinion in Immunology 2002, 14:52-65).
Salmeron et al. (J. of Immunology, vol. 147, pp. 3047-3052, 1991). (Year: 1991).
Schlitt, H.J., et al., "Different Activation States of Human Lymphocytes after Antibody-Mediated Stimulation via CD3 and the α/β T-Cell Receptor," Scandinavian Journal of Immunology, Dec. 1990, vol. 32, Issue 6, pp. 717-726.
Schodin et al. (Molecular Immunology, vol. 33, No. 9, pp. 819-829, 1996).
Shalaby et al. (J Exp Med. Jan. 1, 1992;175(1):217-25).
Van Der Merwe et al., Curr Biol. Jan. 1, 1995;5(1):74-84.
Weber et al. (Proc Natl Acad Sci U S A. Dec. 27, 2005;102(52):19033-8).
Wen et al., Cancer Immunol Immunother (2008) 57:1781-1794.
Willemsen et al. (Cytometry Part A, 73A: 1093-1099, 2008).
Willemsen, R., et al., "Selection of Human Antibody Fragments Directed Against Tumor T-Cell Epitopes for Adoptive T-Cell Therapy," 2008, Cytometry Part A, 73A:1093-1099.
Willemsen, R., et al., "T Cell Retargeting with MHC Class I-Restricted Antibodies: The CD28 Costimulatory Domain Enhances Antigen-Specific Cytotoxicity and Cytokine Production," The Journal of Immunology, 2005, pp. 7853-7858, vol. 174.
Woo et al. (Protein Expression and Purification 58 (2008) 1-11).
Written Opinion for PCT/GB2010/000988 dated Oct. 7, 2010.
Zhu et al. (Int J Cancer. Jul. 28, 1995;62(3):319-24).
Zhu et al., Biochemistry 2002, 41, 12163-12170.
Argos, P., "An investigation of oligopeptides linking domains in protein tertiary structures and possible candidates for general gene fusion," *Journal of Molecular Biology*, vol. 211, Issue 4, Feb. 20, 1990, pp. 943-958.
Boulter et al., "Stable, soluble T-cell receptor molecules for crystallization and therapeutics," *Protein Engineering, Design and Selection*, vol. 16, Issue 9, Sep. 1, 2003, pp. 707-711.
Card et al., "A soluble single-chain T-cell receptor IL-2 fusion protein retains MHC-restricted peptide specificity and IL-2 bioactivity," Apr. 2004, vol. 53, Issue 4, pp. 345-357.
Denkberg et al., "Recombinant antibodies with T-cell receptor-like specificity: Novel tools to study MHC class I presentation," *Autoimmunity Reviews*, vol. 5, Issue 4, Apr. 2006, pp. 252-257.
Molloy et al., "Soluble T cell receptors: novel immunotherapies," *Current Opinion in Pharmacology*, vol. 5, Issue 4, Aug. 2005, pp. 438-443.
Notice of opposition, European patent application No. EP16176249.7, dated Jan. 23, 2019, 159 pages.
Ortiz-Sanchez et al., "Antibody-cytokine fusion proteins: applications in cancer therapy," *Expert Opin Biol. Ther.* 2008, 8(5), pp. 609-632.
Peng et al., "A Single-Chain IL-12 IgG3 Antibody Fusion Protein Retains Antibody Specificity and IL-12 Bioactivity and Demonstrates Antitumor Activity," *The Journal of Immunology*, vol. 1, Issue 1, Jul. 1, 1999, pp. 250-258.
Wen et al., "Targeting activity of a TCR/IL-2 fusion protein against established tumors," *Cancer Immunology, Immunotherapy*, Dec. 2008, vol. 57, Issue 12, pp. 1781-1794.
Davis, C. et al., "Immunocytokines: amplification of anti-cancer immunity," *Cancer Immunology, Immunotherapy*, vol. 52, Issue 5, May 2003, pp. 297-308.
Klechevsky, E. et al., "Antitumor Activity of Immunotoxins with T-Cell Receptor-like Specificity against Human Melanoma Xenografts," *Cancer Research*, vol. 68, No. 15, Aug. 1, 2008, pp. 6360-6367.
Notice of opposition, European Patent Application No. 16176246.3, dated May 8, 2019, 42 pages.
Pule, M. et al., "Artificial T-Cell Receptors," *Cytotherapy*, vol. 5, No. 3, Jan. 2003, pp. 211-226.
Ruf, P. et al., "Induction of a long-lasting antitumor immunity by a trifunctional bispecific antibody," *Blood*, vol. 98, No. 8, Oct. 15, 2001, pp. 2526-2534.
Sadelain, M. et al., "The promise and potential pitfalls of chimeric antigen receptors," *Current Opinion in Immunology*, vol. 21, No. 2, Apr. 2009, pp. 215-223.
Xiong, C-Y. et al., "Development of tumor targeting anti-MUC-1 multimer: effects of di-scFv unpaired cysteine location of PEGylation and tumor binding," *Protein Engineering, Design & Selection*, vol. 19, No. 8, 2006, pp. 359-367.

\* cited by examiner

FIG 1

SEQ ID No: 1 - NY-ESO TCR alpha chain amino acid sequence

SEQ ID No: 2 - NY-ESO beta chain amino acid sequence:

NAGVTQTPKFQVLKTGQSMTLQCAQDMNHEYMSWYRQD

PGMGLRLIHYSVAIQTTDQGEVPNGYNVSRSTIEDFPLRL

LSAAPSQTSVYFCASSYLGNTGELFFGEGSRLTVLEDLKN

VFPPEVAVFEPSEAEISHTQKATLVCLATGFYPDHVELSW

WVNGKEVHSGV<u>C</u>TDPQPLKEQPALNDSRYALSSRLRVSA

TFWQDPRNHFRCQVQFYGLSENDEWTQDRAKPVTQIVSA

EAWGRAD

FIG 3

SEQ ID NO: 3 - UCHT-1 scFv amino acid sequence (with the intralinker underlined):

```
          10          20          30          40
           *           *           *           *
DIQMTQSPSSLSASVGDRVTITCRASQDIRNYLNWYQQKP
          50          60          70          80
           *           *           *           *
GKAPKLLIYYTSRLESGVPSRFSGSGSGTDYTLTISSLQPE
          90         100         110         120
           *           *           *           *
DFATYYCQQGNTLPWTFGQGTKVEIK RTSGPGDGGKGGP
                     130         140         150
                      *           *           *
GKGPGGEGTKGTGPGG EVQLVESGGGLVQPGGSLRLSC
         160         170         180         190
           *           *           *           *
AASGYSFTGYTMNWVRQAPGKGLEWVALINPYKGVSTYN
         200         210         220         230
           *           *           *           *
QKFKDRFTISVDKSKNTAYLQMNSLRAEDTAVYYCARSGY
         240         250
           *           *
YGDSDWYFDVWGQGTLVTVSS
```

FIG 8

SEQ ID No: 7 - Chimeric Wong insulin TCR alpha chain amino acid sequence

SEQ ID No: 9 - Chimeric Wong insulin TCR beta chain amino acid sequence

SEQ ID No: 10 - Murine IL-4 aminoacid sequence:

HIHGCDKNHLREIIGILNEVTGEGTPCTEMDVPNVLTATKNTTESELVCRASKVLRIF
YLKHGKTPCLKKNSSVLMELQRLFRAFRCLDSSISCTMNESKSTSLKDFLESLKSIM
QMDYS

FIG 11

SEQ ID No: 11 - Murine IL-13 aminoacid sequence:

GPVPRSVSLPLTLKELIEELSNITQDQTPLCNGSMVWSVDLAAGGFCVALDSLTNIS
NCNAIYRTQRILHGLCNRKAPTTVSSLPDTKIEVAHFITKLLSYTKQLFRHGPF

FIG 16

SEQ ID No: 14 – Amino acid sequence of NY-ESO TCR beta chain fused to anti-CD3 scFv, anti-CD3 scFv being fused to the C-terminal end of the TCR beta chain via a peptide linker:

NAGVTQTPKFQVLKTGQSMTLQCAQDMNHEYMSWYRQDPGMGLRLIHYSVAIQTT
DQGEVPNGYNVSRSTIEDFPLRLLSAAPSQTSVYFCASSYLGNTGELFFGEGSRLT
VLEDLKNVFPPEVAVFEPSEAEISHTQKATLVCLATGFYPDHVELSWWVNGKEVHS
GVCTDPQPLKEQPALNDSRYALSSRLRVSATFWQDPRNHFRCQVQFYGLSENDE
WTQDRAKPVTQIVSAEAWGRAD<u>GGGGS</u>AIQMTQSPSSLSASVGDRVTITCRASQD
IRNYLNWYQQKPGKAPKLLIYYTSRLESGVPSRFSGSGSGTDYTLTISSLQPEDFAT
YYCQQGNTLPWTFGQGTKVEIKGGGGSGGGGSGGGGSGGGGSGGGGSEVQLVE
SGGGLVQPGGSLRLSCAASGYSFTGYTMNWVRQAPGKGLEWVALINPYKGVSTY
NQKFKDRFTISVDKSKNTAYLQMNSLRAEDTAVYYCARSGYYGDSDWYFDVWGQ
GTLVTVSS

FIG 17

SEQ ID No: 15 – Amino acid sequence of NY-ESO TCR beta chain fused to anti-CD3 scFv, anti-CD3 scFv being fused to the N-terminal end of the TCR beta chain via a peptide linker:

AIQMTQSPSSLSASVGDRVTITCRASQDIRNYLNWYQQKPGKAPKLLIYYTSRLESG
VPSRFSGSGSGTDYTLTISSLQPEDFATYYCQQGNTLPWTFGQGTKVEIKGGGGS
GGGGSGGGGSGGGGSEVQLVESGGGLVQPGGSLRLSCAASGYSFTGYTM
NWVRQAPGKGLEWVALINPYKGVSTYNQKFKDRFTISVDKSKNTAYLQMNSLRAE
DTAVYYCARSGYYGDSDWYFDVWGQGTLVTVSS<u>GGGGS</u>NAGVTQTPKFQVLKTG
QSMTLQCAQDMNHEYMSWYRQDPGMGLRLIHYSVAIQTTDQGEVPNGYNVSRSTI
EDFPLRLLSAAPSQTSVYFCASSYLGNTGELFFGEGSRLTVLEDLKNVFPPEVAVFE
PSEAEISHTQKATLVCLATGFYPDHVELSWWVNGKEVHSGVCTDPQPLKEQPALN
DSRYALSSRLRVSATFWQDPRNHFRCQVQFYGLSENDEWTQDRAKPVTQIVSAEA
WGRAD

BIFUNCTIONAL POLYPEPTIDES

CROSS REFERENCE TO RELATED APPLICATIONS

This application is a continuation of U.S. application Ser. No. 16/151,144, filed Oct. 3, 2018, which is a continuation of U.S. application Ser. No. 13/319,597, filed Apr. 5, 2012, now U.S. Pat. No. 10,130,721, which is the National Stage of International Application No. PCT/GB2010/000988, filed May 19, 2010, which claims the benefit of and priority to Great Britain Patent Application No. 0908613.3, filed May 20, 2009, each of which is herein incorporated in its entirety by reference.

SEQUENCE LISTING

The instant application contains a Sequence Listing which has been submitted electronically in ASCII format and is hereby incorporated by reference in its entirety. Said ASCII copy, created on Apr. 4, 2019, is named 42799US_CRF_SequenceListing.txt and is 23,605 bytes in size.

FIELD OF THE INVENTION

This invention relates to a bifunctional polypeptide comprising a specific binding partner for a peptide-MHC epitope, such as an antibody or a T cell receptor ("TCR"), and an immune effector, such as an antibody or a cytokine, the immune effector part being linked to the N-terminus of the peptide-MHC binding part.

BACKGROUND TO THE INVENTION

TCRs mediate the recognition of Specific Major Histocompatibility Complex (MHC)-peptide complexes ("pMHC complexes") which are presented as epitopes on antigen presenting cells (APC), and TCRs mediate the recognition of such pMHC epitopes by T cells. As such TCRs are essential to the functioning of the cellular arm of the immune system. Antibodies are also known which specifically bind pMHC epitopes presented by antigen presenting cells (see for example: Neethling F A. et al., *Vaccine* (2008) 26 (25): 3092-102). There are antigen-binding fragment (Fab) antibodies (see for example: Chames P. et al., *Proc Natl Acad Sci USA* (2000) 97 (14): 7969-74; Willemsen R A. et al., *J Immunol* (2005) 174 (12): 7853-8; Willemsen R. et al., *Cytometry A* (2008) 73 (11): 1093-9) or single-chain antibody fragments (scFv) (see for example: Denkberg G. et al., *J Immunol* (2003) 171 (5): 2197-207; Marget M. e al., *Mol Immunol* (2005) 42 (5): 643-9) which specifically bind pMHC epitopes.

The native TCR is a heterodimeric cell surface protein of the immunoglobulin superfamily which is associated with invariant proteins of the CD3 complex involved in mediating signal transduction. TCRs exist in αβ and γδ forms, which are structurally similar but have quite distinct anatomical locations and probably functions. The MEW class I and class II ligands are also immunoglobulin superfamily proteins but are specialised for antigen presentation, with a highly polymorphic peptide binding site which enables them to present a diverse array of short peptide fragments at the APC cell surface.

The extracellular portion of native heterodimeric αβ TCRs consist of two polypeptides (the α and β chains) each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. CDR3 of αβ TCRs interact with the peptide presented by MEW, and CDRs 1 and 2 of αβ TCRs interact with the peptide and the MEW. The diversity of TCR sequences is generated via somatic rearrangement of linked variable (V), diversity (D), joining (J), and constant genes (C).

Functional a chain polypeptides are formed by rearranged V-J-C regions, whereas β chains consist of V-D-J-C regions. The extracellular constant domain has a membrane proximal region and an immunoglobulin region. There is a single a chain constant domain, known as TRAC. The β chain constant domain is composed of one of two different β constant domains, known as TRBC1 and TRBC2 (IMGT nomenclature). There are four amino acid changes between these β constant domains. These changes are all within exon 1 of TRBC1 and TRBC2: $N_4K_5 \rightarrow K_5N_5$ and $F_{37} \rightarrow Y$ (IMGT numbering, differences TRBC1→TRBC2), the final amino acid change between the two TCR β chain constant regions being in exon 3 of TRBC1 and TRBC2: $V_1 \rightarrow E$.

A number of constructs have been devised to date for the production of recombinant TCRs. These constructs fall into two broad classes, single-chain TCRs and dimeric TCRs. Single-chain TCRs (scTCRs) are artificial constructs consisting of a single amino acid strand, which like native heterodimeric TCRs bind to MHC-peptide complexes. scTCRs can consist of a combination of TCR α and β variable regions (Vα and Vβ respectively) and TCR α and β constant regions (Cα and Cβ respectively), linked by a linker sequence (L) in several possible orientations, for example, but not limited to, the following Vα-L-Vβ, Vβ-L-Vα, Vα-Cα-L-Vβ or Vβ-Cβ-L-Vα.

A number of papers describe the production of TCR heterodimers which include the native disulphide bridge which connects the respective subunits. However, although such TCRs can be recognised by TCR-specific antibodies, none have been shown to recognise its native ligand at anything other than relatively high concentrations and/or were not stable.

In WO 03/020763 a soluble TCR is described which is correctly folded so that it is capable of recognising its native ligand, is stable over a period of-time, and can be produced in reasonable quantities. This TCR comprises a TCR α chain extracellular domain dimerised to a TCR β chain extracellular domain respectively, by means of an inter-chain disulfide bond between cysteines introduced into the constant regions of the respective chains.

Specific pMHC binding partners, ie antibodies specific for pMHC epitopes, and TCRs of both the heterodimeric and single chain type, have been proposed as targeting vectors for the delivery of therapeutic agents to antigen presenting cells. For that purpose, the therapeutic agent is required to be associated with the pMHC-binding partner in some way. Therapeutic agents which have been suggested for such targeted delivery in association with pMHC-binding partners include antibodies (see for example: Mosquera L A. et al., *J Immunol* (2005) 174 (7): 4381-8), cytokines (see for example: Belmont H J. et al., *Clin Immunol* (2006) 121 (1): 29-39; Wen J. et al. *Cancer Immunol Immunother* (2008) 57 (12): 1781-94), and cytotoxic agents. Where the therapeutic agent is a polypeptide, the means of association with the pMHC binding partner may be by peptidic fusion, either direct fusion or fusion via a linker sequence, to the pMHC binding partner. In those cases, there are essentially only two fusion possibilities. In the case of single chain antibodies or TCRs, fusion can in principle be at the C- or N-terminus of the TCR chain; In the case of heterodimeric antibodies or TCRs, the fusion can in principle be at the C- or N-terminus of either chain. In practice however, it appears that all known examples of pMHC binding partner-therapeutic agent fusions have been with the therapeutic agent fused to the C-terminus (see for example: Mosquera L A. et al., *J Immunol* (2005) 174 (7): 4381-8; Belmont H J. et al., *Clin Immunol* (2006) 121 (1): 29-39; Wen J. et al., *Cancer Immunol Immunother* (2008) 57 (12): 1781-94). This is because the functionality of an antibody or TCR, whether single chain or heterodimeric, depends on correct folding and orientation of the variable regions. Fusion of the therapeutic agent to the N-terminus of the pMHC binding partner places it ahead of one of the variable regions, and there has been an assumption in the art that the therapeutic agent located at the N-terminus will interfere with binding of the antibody or TCR to the pMHC complex, thereby reducing its binding efficiency.

SUMMARY OF THE INVENTION

Contrary to that assumption in the art, it has now been found that bifunctional molecules wherein an immune effector part is fused to the N-terminus of a pMHC-binding partner are more effective in their induction of the relevant immune response that the corresponding construct wherein the fusion is to the C-terminus of the pMHC-binding partner. This enhanced immune response of the N-fused construct achieved despite the similar pMHC binding affinities of the N- and C-fused version.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1 shows the amino acid sequence of the alpha chain of an NY-ESO TCR, in which C162 (using the numbering of SEQ ID No: 1) replaces T48 of its TRAC constant region.

FIG. 2 shows the amino acid sequence of the beta chain NY ESO-TCR, in which C170 (using the numbering of SEQ ID No: 2) replaces S57 of its TRBC2 constant region.

FIG. 3 shows the amino acid sequence of an anti CD3 UCHT-1 scFv antibody, with its intralinker sequence underlined.

FIG. 8 shows the amino acid sequence of the alpha chain of a TCR having the property of binding to a murine insulin-derived peptide, LYLVCGERG (SEQ ID NO: 8), presented by the murine H-2K$^d$ complex, LYLVCGERG-H-2K$^d$ ("LYLVCGERG" disclosed as SEQ ID NO: 8), in which C158 (using the numbering of SEQ ID No: 7) replaces T48 of its TRAC constant region.

FIG. 9 shows the amino acid sequence of the beta chain of the same TCR which binds the murine LYLVCGERG-H-2Kd complex ("LYLVCGERG" disclosed as SEQ ID NO: 8), in which C171 (using the numbering of SEQ ID No: 9) replaces S57 of its TRBC2 constant region.

FIG. 10 shows the amino acid sequence of a murine IL-4 polypeptide represented by SEQ ID No: 10.

FIG. 11 shows SEQ ID No: 11 which is the amino acid sequence of a murine IL-13 polypeptide.

FIG. 16 shows the amino acid sequence (SEQ ID No:14) of the beta chain of FIG. 2 with the N-terminus of an anti-CD3 scFv fused to the C-terminus of the TCR beta chain via another peptide linker sequence (underlined).

FIG. 17 shows the amino acid sequence (SEQ ID No:15) of the beta chain of FIG. 2 with the C-terminus of an anti-CD3 scFv fused to the N-terminus of the TCR beta chain via the same peptide linker sequence as in SEQ ID No 14 (again underlined).

DETAILED DESCRIPTION OF THE INVENTION

Figure 4:
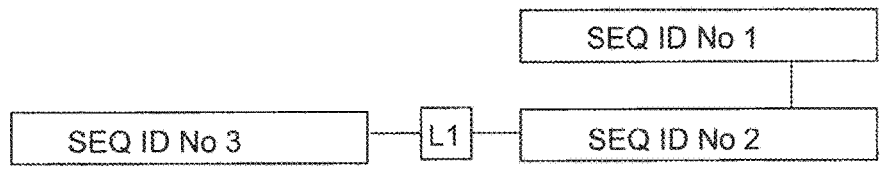
FIG. 4 shows in block diagram form the structure of a soluble NY-ESO αβ TCR having the α chain SEQ ID No: 1 and the β chain SEQ ID No: 2, and having the anti CD3 UCHT-1 scFv antibody SEQ ID No: 3 fused at the N terminus of the TCR β chain SEQ ID No: 2 via a linker sequence L1 namely GGEGS (SEQ ID No: 4).

Accordingly, the present invention provides a bifunctional molecule comprising a polypeptide binding partner specific for a given pMHC epitope, and an immune effector polypeptide, the N-terminus of the pMHC binding partner being linked to the C-terminus of the immune effector polypeptide, PROVIDED THAT the said polypeptide binding partner is not a T-cell receptor comprising the alpha chain SEQ ID No: 7 and the beta chain SEQ ID No: 9.

As mentioned, the polypeptide pMHC binding partner may be an antibody or a TCR. Thus in one embodiment of the invention the pMHC binding partner is a heterodimeric TCR polypeptide pair, or a single chain TCR polypeptide, and the N-terminus of the α or β chain of the heterodimeric TCR polypeptide pair, or the N-terminus of the scTCR polypeptide, is linked to a C-terminal amino acid of the immune effector polypeptide.

Linkage of the pMHC binding partner and the immune effector polypeptide may be direct, or indirect via linker sequence. Linker sequences are usually flexible, in that they are made up of amino acids such as glycine, alanine and serine which do not have bulky side chains likely to restrict flexibility. Usable or optimum lengths of linker sequences are easily determined in the case of any given pMHC binding partner-immune effector construct. Often the linker sequence will by less than about 12, such as less that 10, or from 5-10 amino acids in length.

In some embodiments of the invention the pMHC binding partner is a heterodimeric αβ TCR polypeptide pair wherein the α and β polypeptides each have TCR variable and constant regions, but lack TCR transmembrane and cytoplasmic regions. The TCR part in such cases is soluble. In particularly preferred embodiments of this type, a non-native disulfide bond between residues of the constant regions of TCR α and β polypeptides is present. In particular the constant regions of the α and β polypeptides may be linked by a disulfide bond between cysteine residues substituted for Thr 48 of exon 1 of TRAC1 and Ser 57 of exon 1 of TRBC1 or TRBC2, or by the native disulfide bond between Cys4 of exon 2 of TRAC*01 and Cys2 of exon 2 of TRBC1 or TRBC2.

In other embodiments of the invention, the pMHC binding partner is a single chain αβ TCR polypeptide of the Vα-L-Vβ, Vαβ-L-Vα, Vα-Cα-L-Vβ, or Vα-L-Vβ-Cβ type wherein Vα and Vβ are TCR α and β variable regions respectively, Cα and Cβ a are TCR α and β constant regions respectively, and L is a linker sequence.

Immune effector polypeptides are known. They are molecules which induce or stimulate an immune response, through direct or indirect activation of the humoural or cellular arm of the immune system, such as by activation of T-cells. Examples include: IL-1, IL-1a, IL-3, IL-4, IL-5, IL-6, IL-7, IL-10, IL-11, IL-12, IL-13, IL-15, IL-21, IL-23, TGF-β, IFN-γ, TNFα, Anti-CD2 antibody, Anti-CD3 antibody, Anti-CD4 antibody, Anti-CD8 antibody, Anti-CD44 antibody, Anti-CD45RA antibody, Anti-CD45RB antibody, Anti-CD45RO antibody, Anti-CD49a antibody, Anti-CD49b antibody, Anti-CD49c antibody, Anti-CD49d antibody, Anti-CD49e antibody, Anti-CD49f antibody, Anti-CD16 antibody, Anti-CD28 antibody, Anti-1L-2R antibodies, Viral proteins and peptides, and Bacterial proteins or peptides. Where the immune effector polypeptide is an antibody it may be scFv antibody, one such being an anti-CD3 scFv. Examples of anti-CD3 antibodies include but are not limited to OKT3, UCHT-1, BMA031 and 12F6.

The principles of the invention are illustrated by the following Examples.

Example A. Preparation of Soluble αβ TCRs Having Effector Polypeptides Fused to the C- or N-Terminus of the TCR β Chain A1. Soluble NY-ESO TCR with Anti-CD3 Antibody as Effector Polypeptide The soluble NY-ESO TCR of this example has the property of binding to the SLLMWITQV peptide (SEQ ID NO: 16) when presented on an HLA-A2 molecule.

Figure 1:
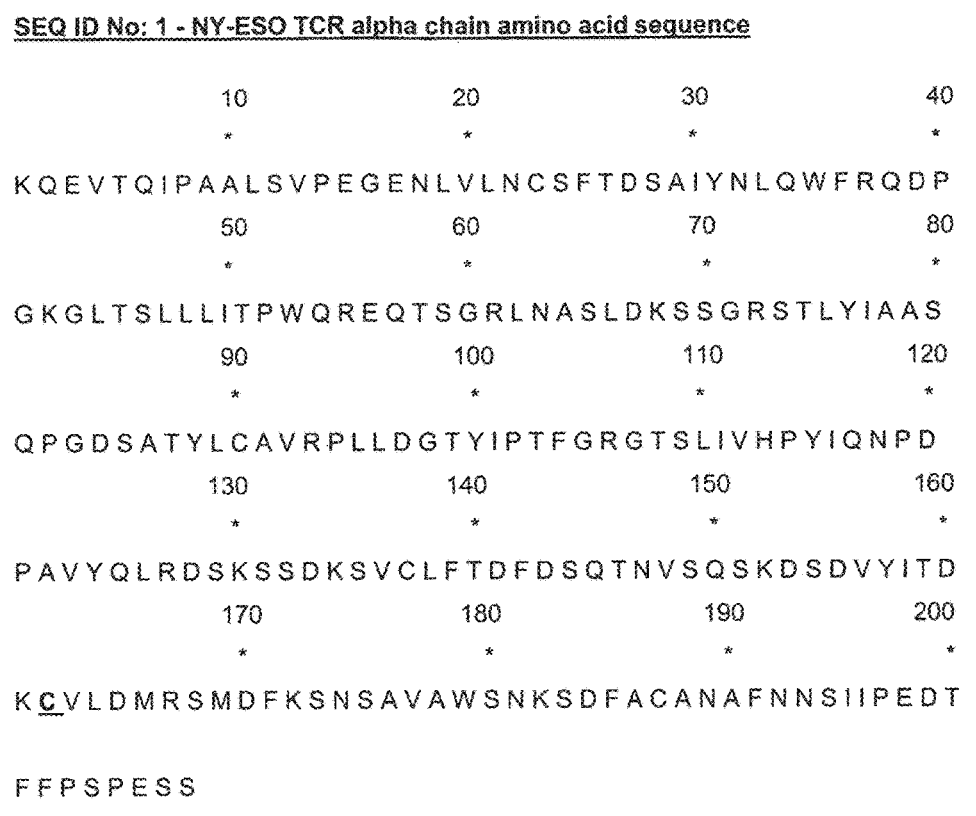

SEQ ID No: 1 (FIG. 1) is the amino acid sequence of the alpha chain of an NY-ESO TCR, in which C162 (using the numbering of SEQ ID No: 1) replaces T48 of its TRAC constant region.

SEQ ID No: 2 (FIG. 2) is the amino acid sequence of the beta chain NY ESO-TCR, in which C170 (using the numbering of SEQ ID No: 2) replaces S57 of its TRBC2 constant region.

SEQ ID No: 3 (FIG. 3) is the amino acid sequence of an anti CD3 UCHT-1 scFv antibody, with its intralinker sequence underlined.

FIG. 4 shows in block diagram form the structure of a soluble NY-ESO αβ TCR having the α chain SEQ ID No: 1 and the β chain SEQ ID No: 2, and having the anti CD3 UCHT-1 scFv antibody SEQ ID No: 3 fused at the N terminus of the TCR β chain SEQ ID No: 2 via a linker sequence L1 namely GGEGS (SEQ ID No: 4).

SEQ ID No: 14 (FIG. 16) is the amino acid sequence of the beta chain of FIG. 2 with the N-terminus of an anti-CD3 scFv fused to the C-terminus of the TCR beta chain via another peptide linker sequence (underlined).

SEQ ID No: 15 (FIG. 17) is the amino acid sequence of the beta chain of FIG. 2 with the C-terminus of an anti-CD3 scFv fused to the N-terminus of the TCR beta chain via the same peptide linker sequence as in SEQ ID No 14 (again underlined).

The construct of FIG. 4 was prepared as follows:

Ligation

Synthetic genes encoding (a) the TCR α chain SEQ ID No: 1 and (b) the fusion sequence of SEQ ID No: 2 and EQ ID No: 3, were separately ligated into pGMT7-based expression plasmids, which contain the T7 promoter for high level expression in *E. coli* strain BL21-DE3(pLysS) (Pan et al., *Biotechniques* (2000) 29 (6): 1234-8.

Expression

The expression plasmids were transformed separately into *E. coli* strain BL21 (DES) Rosetta pLysS, and single ampicillin-resistant colonies were grown at 37° C. in TYP (ampicillin 100 μg/ml) medium to $OD_{600}$ of ~0.6-0.8 before inducing protein express with 0.5 mM IPTG. Cells were harvested three hours post-induction by centrifugation for 30 minutes at 4000 rpm in a Beckman J-6B. Cell pellets were lysed with 25 ml Bug Buster (NovaGen) in the presence of $MgCl_2$ and DNase. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl pH 8.0, 0.5% Triton-X100, 200 mM NaCl, 10 mM NaEDTA) before being pelleted by centrifugation for 15 minutes at 13000 rpm in a Beckman J2-21. Detergent and salt was then removed by a similar wash in the following buffer: 50 mM Tris-HCl pH 8.0, 1 mM NaEDTA. Finally, the inclusion bodies were divided into 30 mg aliquots and frozen at −70° C.

Refolding

Approximately 20 mg of TCR α chain and 40 mg of scFv-TCR β chain solubilised inclusion bodies were thawed from frozen stocks, diluted into 20 ml of a guanidine solution (6 M Guanidine-hydrochloride, 50 mM Tris HCl pH 8.1, 100 m NaCl, 10 mM EDTA, 20 mM OTT), and incubated in a 37° C. water bath for 30 min-1 hr to ensure complete chain de-naturation. The guanidine solution containing fully reduced an denatured TCR chains was then injected into 1 litre of the following refolding buffer: 100 mM Tris pH 8.1, 400 mM L-Arginine, 2 mM EDTA, 5M Urea. The redox couple (cysteamine hydrochloride and cystamine dihydrochloride (to final concentrations of 16 mM and 1.8 mM, respectively)) were added approximately 5 minutes before addition of the denatured TCR α and scFv-TCR β chains. The solution was left for ~30 minutes. The refolded scFv-TCR was dialysed in dialysis tubing cellulose membrane (Sigma-Aldrich; Product No. D9402) against 10 L H$_2$O for 18-20 hours. After this time, the dialysis buffer was changed twice to fresh 10 mM Tris pH 8.1 (10 L) and dialysis was continued at 5° C.±3° C. for another ~8 hours. Soluble and correctly folded scFv-TCR was separated from misfolded, degradation products a impurities by a 3-step purification method as described below. The second purification step can either be an ion exchange chromatography or an affinity chromatography, depending on the pl of the soluble. anti-CD3 scFv-TCR fusion.

First Purification Step

The dialysed refold (in 10 mM Tris pH8.1) was loaded onto a POROS 50HQ anion exchange column and the bound protein eluted with a gradient of 0-500 mM NaCl over 6 column volumes using an Akta purifier (GE Healthcare). Peak fractions (eluting at a conductivity ~20 mS/cm) were stored at 4° C. Peak fractions were analysed by Instant Blue Stain (Novexin) stained SDS-PAGE before being pooled.

Second Purification Step

Ion Exchange Chromatography

Cation Exchange Purification:

The anion exchange pooled fractions were buffer exchanged by dilution with 20 mM IVIES pH6-6.5, depending on the pl of the scFv-TCR fusion. The soluble and correctly folded scFv-TCR was separated from misfolded, degradation products and impurities by loading the diluted pooled fractions (in 20 mM IVIES pH6-6.5) onto a POROS 50HS cation exchange column and eluting bound protein with a gradient of 0-500 mM NaCl over 6 column volumes using an Akta purifier (GE Healthcare). Peak fractions (eluting at a conductivity ~10 mS/cm) were stored at 4° C.

Alternatively, ion exchange purification using hydroxyapatite matrix can be used a explained below.

Hydroxyapatite Chromatography:

The anion exchange pooled fractions were buffer exchanged by dilution with 10 mM NaH$_2$PO$_4$ pH6.0. The soluble and correctly folded scFv-TCR was separated from misfolded, degradation products and impurities by loading the diluted pooled fractions (in 10 mM NaH$_2$PO$_4$ pH6.0) onto a hydroxyapatite column and eluting bound protein with a gradient of 10-500 mM NaH$_2$PO$_4$/1M NaCl over 6 column volumes using an Akta purifier (GE Healthcare). Peak fractions (eluting at a conductivity ~20 mS/cm) were stored at 4° C.

Affinity Chromatography

For some scFv-TCR fusions with a pl close to 6-6.5, the ion exchange step cannot be used but can be replaced by an affinity chromatography step. The protein L affinity chromatography column (Pierce, product number 89928) isolates and purifies certain immunoglobulin classes via their kappa light chains. Protein L can also binds sing chain variable fragments (scFv). The anion exchange pooled fractions were buffer exchanged by dilution with PBS/0.02% sodium azide. The soluble and correctly folded scFv-TCR was separated from misfolded, degradation products and impurities by loading the diluted pooled fractions onto a Protein L column and eluting bound protein with a gradient of 0-25 mM Glycine pH2.3/0.02% sodium azide over 3 column volumes using an Akta purifier (GE Healthcare). The scFv-TCR eluted very late in gradient and the pH of the eluted fractions was neutralized by addition of Tris pH8 1 (100 mM Tris pH8.1 final concentration). The peak fractions were stored at 4° C.

Final Purification Step

Figure 5:
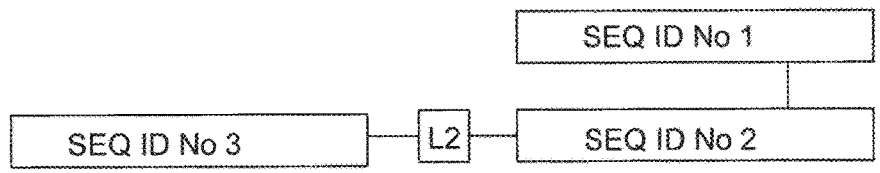
FIG. 5 shows in block diagram form the structure of a soluble NY-ESO αβ TCR having the α chain SEQ ID No: 1 and the β chain SEQ ID No: 2, and having the anti CD3 UCHT-1 scFv antibody SEQ ID No: 3 fused at the N terminus of the TCR β chain SEQ ID No: 2 via a linker sequence L2 namely AHHSEDPSSKAPKAP (SEQ ID No: 5).

Peak fractions from second purification step were analysed by Instant Blue Stain (Novexin) stained SDS-PAGE before being pooled. The pooled fractions were then concentrated for the final purification step, when the soluble scFv-TCR was purified and characterised using a Superdex 5200 gel filtration column (GE Healthcare) pre-equilibrated in PBS buffer (Sigma). The peak eluting at a relative molecular weight of approximately 78 kDa was analysed by Instant Blue Stain (Novexin) stained SDS-PAGE before being pooled. In a similar manner to that described for the construct of FIG. 4, the constructs of FIGS. 5, 6 and 7 were prepared:

FIG. 5 shows in block diagram form the structure of a soluble NY-ESO αβ TCR having the α chain SEQ ID No: 1 and the β chain SEQ ID No: 2, and having the anti CD3 UCHT-1 scFv antibody SEQ ID No: 3 fused at the N terminus of the TCR β chain SEQ ID No: 2 via a linker sequence L2 namely AHHSEDPSSKAPKAP (SEQ ID No: 5).

Figure 6:
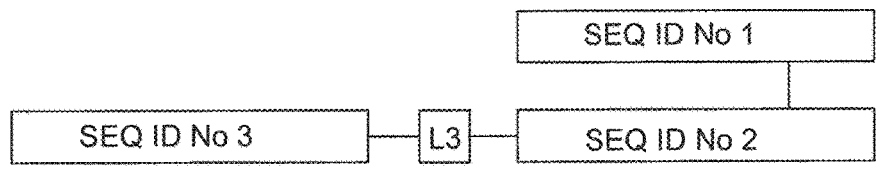
FIG. 6 shows in block diagram form the structure of a soluble NY-ESO αβ TCR having the α chain SEQ ID No: 1 and the β chain SEQ ID No: 2, and having the anti CD3 UCHT-1 scFv antibody SEQ ID No: 3 fused at the N terminus of the TCR β chain SEQ ID No: 2 via a linker sequence L3 namely GGEGGGSEGGGS (SEQ ID No: 6).

FIG. 6 shows in block diagram form the structure of a soluble NY-ESO αβ TCR having the α chain SEQ ID No: 1 and the β chain SEQ ID No: 2, and having the anti CD3 UCHT-1 scFv antibody SEQ ID No: 3 fused at the N terminus of the TCR β chain SEQ ID No: 2 via a linker sequence L3 namely GGEGGGSEGGGS (SEQ ID No: 6).

Figure 7:
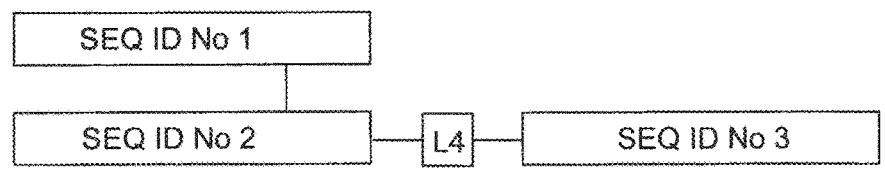
FIG. 7 shows in block diagram form the structure of a soluble NY-ESO αβ TCR having the α chain SEQ ID No: 1 and the β chain SEQ ID No: 2, and having the anti CD3 UCHT-1 scFv antibody SEQ ID No: 3 fused at the C terminus of the TCR β chain SEQ ID No: 2 via a linker sequence L4, which in this case is the single amino acid, S.

FIG. 7 shows in block diagram form the structure of a soluble NY-ESO αβ TCR having the α chain SEQ ID No: 1 and the β chain SEQ ID No: 2, and having the anti CD3 UCHT-1 scFv antibody SEQ ID No: 3 fused at the C terminus of the TCR β chain SEQ ID No: 2 via a linker sequence L4 which in this case is single amino acid S.

In a similar manner to that described for the constructs of FIGS. 4, 5, 6 and 7, the fusion proteins having the TCR α chain SEQ ID No: 1 and the TCR β chain-anti-C scFv SEQ ID No: 14, where the anti-CD3 scFv is fused to the C-terminus of the TCR beta chain, or the TCR α chain SEQ ID No: 1 and the TCR β chain-anti-CD3 scFv SEQ ID No: 15, where the anti-CD3 scFv is fused to the N-terminus of the TCR beta chain, were prepared.

A2. Soluble Chimeric TCR with Cytokines as Effector Polypeptides

Figure 8:
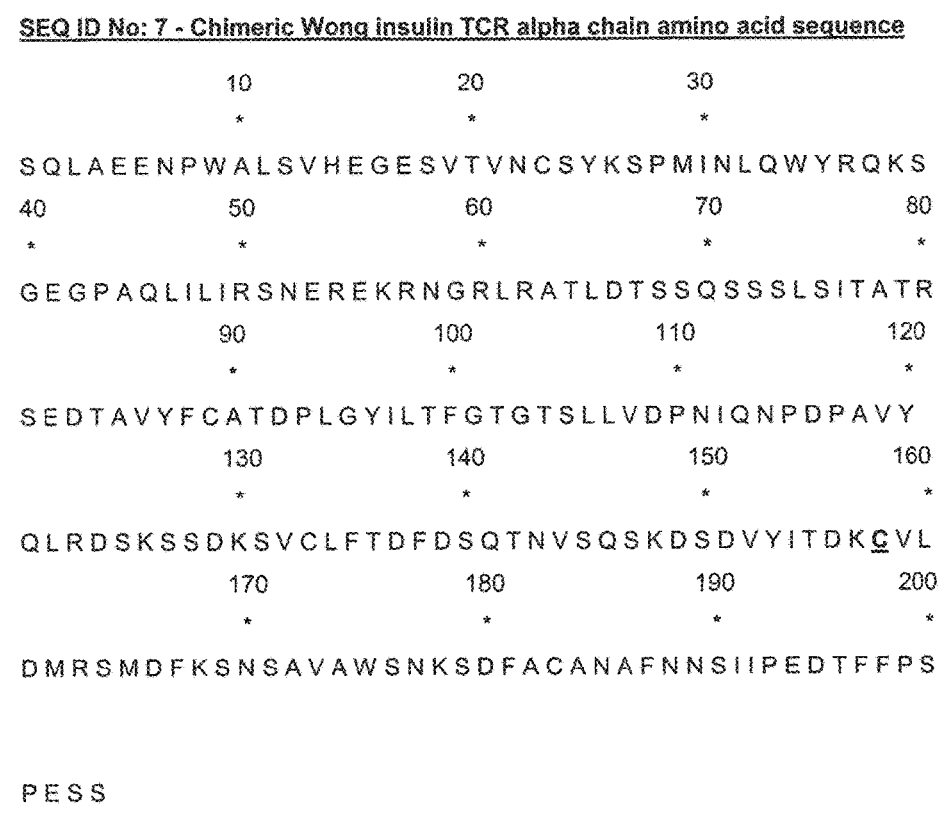

SEQ ID No: 7 (FIG. 8) is the amino acid sequence of the alpha chain of a TCR having the property of binding to a murine insulin-derived peptide, LYLVCGERG (SEQ ID NO: 8), presented by the murine H-2K$^d$ complex. (LYL-VCGERG-H-2K$^d$ ("LYLVCGERG" disclosed as SEQ ID NO: 8)), in which C158 (using the numbering of SEQ ID No: 7) replaces T48 of its TRAC constant region.

SEQ ID No: 9 (FIG. 9) is the amino acid sequence of the beta chain of the same TCR which binds the murine LYL-VCGERG-H-2K$^d$ complex ("LYLVCGERG" disclosed as SEQ ID NO: 8), in which C171 (using the numbering of SEQ ID No: 9) replaces S57 of its TRBC2 constant region.

The SEQ ID No: 7 and 9 TCR is a chimeric TCR consisting of an alpha and a beta TCR chain, each comprising a murine variable region and a human constant region. The chimeric version of the TCR was constructed to improve refolding problems encountered with the fully murine TCR; and the chimeric TCR was shown to have the same affinity as the murine TCR for the murine insulin-derived peptide-murine H-2K$^d$ complex.

SEQ ID No: 10 (FIG. 10) is the amino acid sequence of a murine IL-4 polypeptide.

SEQ ID No: 11 (FIG. 11) is the amino acid sequence of a murine IL-13 polypeptide.

Figure 12:
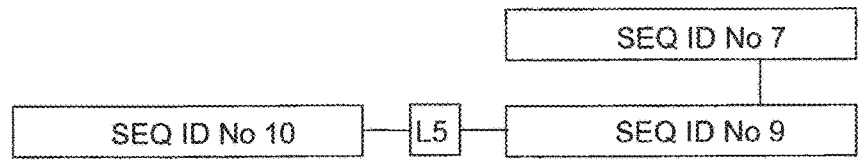
FIG. 12 shows in block diagram form the structure of a soluble chimeric insulin αβ TCR having the α chain SEQ ID No: 7 and the β chain SEQ ID No: 9, and having murine IL-4 SEQ ID No: 10 fused at the N terminus of the TCR β chain SEQ ID No: 9 via the linker sequence L5, namely GGEGGGP (SEQ ID No: 12).

FIG. 12 shows in block diagram form the structure of a soluble chimeric insulin αβ TCR having the α chain SEQ ID No: 7 and the β chain SEQ ID No: 9, and having murine IL-4 SEQ ID No: 10 fused at the N terminus of the TCR β chain SEQ ID No: 9 via the linker sequence L5, namely GGEGGGP (SEQ ID No: 12).

Figure 13:
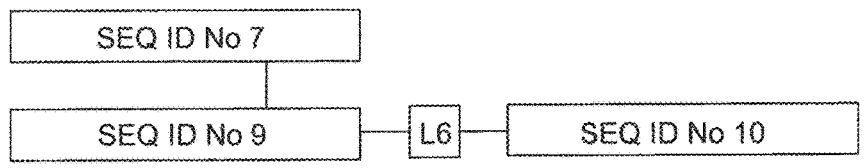
FIG. 13 shows in block diagram form the structure of a soluble chimeric insulin αβ TCR having the α chain SEQ ID No: 7 and the β chain SEQ ID No: 9, and having the murine IL-4 (SEQ ID No: 10) fused at the C terminus of the TCR β chain (SEQ ID No: 9) via the linker sequence L6, namely GSGGP (SEQ ID No: 13).

FIG. 13 shows in block diagram form the structure of a soluble chimeric insulin αβ TCR having the α chain SEQ ID No: 7 and the β chain SEQ ID No: 9, and having the murine IL-4 SEQ ID No: 10 fused at the C terminus of the TCR β chain SEQ ID No: 9 via the linker sequence L6, namely GSGGP (SEQ ID No: 13).

Figure 14:
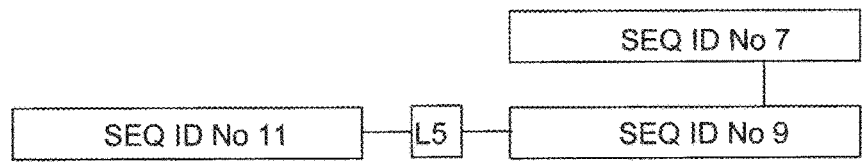
FIG. 14 shows in block diagram form the structure of a soluble chimeric insulin TCR having the α chain SEQ ID No: 7 and the β chain SEQ ID No: 9, and having murine IL-13 (SEQ ID No: 11) fused at the N terminus of the TCR chain (SEQ ID No: 9) via the linker sequence L5, namely GGEGGGP (SEQ ID No: 12).

FIG. 14 shows in block diagram form the structure of a soluble chimeric insulin αβ TCR having the α chain SEQ ID No: 7 and the β chain SEQ ID No: 9, and having murine IL-13 SEQ ID No: 11 fused at the N terminus of the TCR β chain SEQ ID No: 9 via the linker sequence L5, namely GGEGGGP (SEQ ID No: 12).

Figure 15:
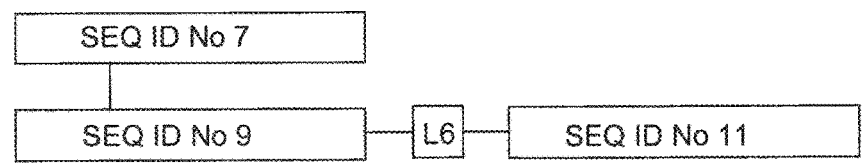
FIG. 15 shows in block diagram form the structure of a soluble chimeric insulin TCR having the α chain SEQ ID No: 7 and the β chain SEQ ID No: 9, and having murine IL-13 (SEQ ID No: 11) fused at the C terminus of the TCR β chain (SEQ ID No: 9) via the linker sequence L6, namely GSGGP (SEQ ID No: 13).

FIG. 15 shows in block diagram form the structure of a soluble chimeric insulin αβ TCR having the α chain SEQ ID No: 7 and the β chain SEQ ID No: 9, and having murine IL-13 SEQ ID No: 11 fused at the C terminus of the TCR β chain SEQ ID No: 9 via the linker sequence L6, namely GSGGP (SEQ ID No: 13).

The constructs of FIGS. 12-15 were prepared as follows.

Ligation

Synthetic genes encoding (a) the TCR α chain SEQ ID No: 7 and (b) the fusion sequence of SEQ ID No: 9 and SEQ ID No: 10 or 11, were separately ligated into pGMT7-based expression plasmids, which contain the T7 promoter for high level expression in *E. coli* strain BL21-DE3(pLysS) (Pan et al., *Biotechniques* (2000) 29 1234-8).

Expression

The expression plasmids containing the TCR α-chain and cytokine-β-chain respectively were transformed separately into *E. coli* strain BL21 (DE3) Rosetta pLysS, and single ampicillin-resistant colonies were grown at 37° C. in TYP (ampicillin 100 μg/ml) medium to $OD_{600}$ of ~0.6-0.8 before inducing protein expression with 0.5 mM IPTG. Cells were harvested three hours post-induction by centrifugation for 30 minutes at 4000 rpm in a Beckman J-6B. Cell pellets were lysed with 25 ml Bug Buster (NovaGen) in the presence of $MgCl_2$ and DNase. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl pH 8.0, 0.5% Triton-X100, 200 mM NaCl, 10 mM NaEDTA) before being pelleted by centrifugation for 15 minutes at 13000 rpm in a Beckman J2-21. Detergent and salt was then removed by a similar wash in the following buffer: 50 mM Tris-HCl pH 8.0, 1 mM NaEDTA. Finally, the inclusion bodies were divided into 30 mg aliquots and frozen at −70° C. Inclusion body protein yield was quantified by solubilising with 6M guanidine-HCl and an OD measurement was taken on a Hitachi U-2001 Spectrophotometer. The protein concentration was the calculated using the theoretical extinction coefficient.

Refolding

Approximately 20 mg of TCR α chain and 40 mg of cytokine-TCR β chain solubilise inclusion bodies were thawed from frozen stocks and diluted into 20 ml of a guanidine solution (6 M Guanidine-hydrochloride, 50 mM Tris HCl pH 8.1, 100 m NaCl, 10 mM EDTA, 10 mM DTT), and incubated in a 37° C. water bath for 30 min-1 hr to ensure complete chain de-naturation. The guanidine solution containing fully reduced and denatured TCR chains was then injected into 1 litre of cold (5-10° C.) refolding buffer: 100 mM Tris pH 8.1, 400 mM L-Arginine, 2 mM EDTA, 5M Urea. The redox couple (cysteamine hydrochloride and cystamine dihydrochloride (to final concentrations 10 mM and 2.5 mM, respectively)) were added approximately 5 minutes before addition of the denatured TCR α and cytokine-TCR β chains. The solution was left for ~30 minutes. The refolded cytokine-TCR was dialysed in dialysis tubing cellulose membrane (Sigma-Aldrich; Product No. 09402) against 10 L $H_2O$ for 18-20 hours. After this time, the dialysis buffer was changed twice to fresh 10 mM Tris pH 8.1 (10 L) and dialysis was continued at 5° C.±3° C. for another ~8 hours.

Purification

Soluble cytokine-TCR fusion was separated from degradation products and impurities by a 3-step purification method at RT as described below.

First Purification Step

The dialysed refold was filtered using a Sartopore 0.2 μm capsule (Sartorius) prior to column purification. Filtered refold was loaded onto a POROS 50HQ anion exchange column and the bound protein eluted with a linear gradient of 0-500 mM NaCl over 6 column volumes using an Akta purifier (GE Healthcare). Peak fractions eluting at 250 mM NaCl, consisting of correctly folded protein, were stored at 4° C. Peak fractions were analysed by Instant Blue Stain (Novexin) stained SDS-PAGE before being pooled.

Second Purification Step

Pooled fractions containing soluble cytokine-TCR were mixed with an equivalent volume of 50 mM Tris/1M $(NH_4)_2SO_4$ pH 8 to give a final concentration of 0.5 M $(NH_4)_2SO_4$ and a conductivity of 75-80 mS/cm at RT. The soluble cytokine-TCR w separated from degradation products and impurities by loading this sample onto pre-equilibrated (50 mM Tris/0.5M $(NH_4)_2SO_4$ pH 8) butyl hydrophobic interaction column (5 ml HiTrap GE Healthcare) and collecting the flow through using an Akta purifier (GE Healthcare). Flow through sample containing soluble cytokine-TCR was analysed by Instant Blue Stain (Novexin) stained SDS-PAGE before being pooled and stored at 4° C.

Final Purification Step

Pooled fractions were diluted with an equivalent volume of 10 mM Tris pH8 and concentrated to 10 ml (concentration of <3 mg/ml). The soluble cytokine-TCR as purified using a Superdex S200 gel filtration column (GE Healthcare) pre-equilibrated in PBS buffer (Sigma). The peak eluting at a relative molecular weight of approximately 63 kDa was analysed by Instant Blue Stain (Novexin) stained SDS-PAGE before being pooled.

Example B. Properties of Soluble αβ TCRs Having Effector Polypeptides Fused to the C- or N-Terminus of the TCR β Chain B1. Soluble NY-ESO TCR with Anti-CD3 Antibody as Effector Polypeptide a. Redirection and Activation of CD8+ T Cells by the Soluble NY-ESO TCR Fused to an Anti-CD3 Antibody Against NY-ESO Peptide-Presenting Cells The following assay was carried out to demonstrate the activation of cytotoxic T lymphocytes (CTLs) by an anti-CD3 scFv-TCR fusion via specific peptide-MHC complex. IFN-γ production, as measured using the ELISPQT assay, was used as a read-out for cytotoxic T lymphocyte (CTL) activation and the evaluation of the potency of the anti-CD3 scFv portion of the fusion.

Reagents

Assay media: 10% FCS (Gibco, Cat#2011-09), 88% RPMI 1640 (Gibco, Cat#42401), 1% glutamine (Gibco Cat#25030) and 1% penicillin/streptomycin (Gibco Cat#15070-063).

Peptide: (SLLMWITQV (SEQ ID NO: 16)) initially dissolved in DMSO (Sigma, cat#D2650) at 4 mg/ml and frozen. T2 cells were pulsed with the described peptide and used as target cells.

Wash buffer: 0.01 M PBS/0.05% Tween 20

PBS (Gibco Cat#10010)

The Human IFNγ ELISPOT PVDF-Enzymatic kit (Diaclone, France; Cat#856.051.020) contains all other reagents required. (Capture and detection antibodies, skimmed milk powder, BSA, streptavidin-alkaline phosphatase and BCIP/NBT solution as well as the Human IFN-γ PVDF ELISPOT 96 well plates)

Method

Target Cell Preparation

The target cells used in this method were either (1) natural epitope-presenting cell (such as Mel624 or Mel526 cells) or (2) T2 cells pulsed with the peptide of interest, described in the reagents section. Sufficient target cells (50 000 cells/well) were washed by centrifugation three times at 1200 rpm, 10 min in a Megafuge 1.0 (Heraeus). Cells were then re-suspended in assay media at $10^6$ cells/ml.

Effector Cell Preparation

The effector cells (T cells) used in this method were either CD8+ T cells (obtained by negative selection (using the CD8 Negative Isolation Kit, Dynal, Cat#113.19) from PBL), T cells from an EBV cell line or PBMCs. Effector cells were defrosted and placed in assay media prior to washing by centrifugation at 1200 rpm, 10 min in a Megafuge 1.0 (Heraeus). Cells were then re-suspended in assay media at a 4× the final required concentration.

Reagent/Test Compound Preparation

Varying concentrations of test compounds (the TCR-anti-CD3 fusions; from 10 nM to 0.03 pM) were prepared by dilution into assay media to give 4× final concentration.

ELISPOTs

Plates were prepared as follows: 100 µl anti-1FN-y capture antibody was diluted in 10 ml sterile PBS per plate. 100 µl of the diluted capture antibody was then aliquoted into each well. The plates were then incubated overnight at 4° C. Following incubation the plates were washed (programme 1, plate type 2, Ultrawash Plus 96-well plate washer; Dynex) to remove the capture antibody. Plates were then blocked by adding 100 µl 2% skimmed milk in sterile PBS to each well and incubating the plates at room temperature for two hours. The skimmed milk was then washed from the plates (programme 1, plate type 2, Ultrawash Plus 96-well plate washer, Dynex) and any remaining wash buffer was removed by flicking and tapping the ELISPOT plates on a paper towel.

The constituents of the assay were then added to the ELISPOT plate in the following order:

50 µl of target cells $10^6$ cells/ml (giving a total of 50 000 target cells/well)

50 µl of reagent (the anti-CD3 scFv-TCR fusions; varying concentrations)

50 µl media (assay media)

50 µl effector cells (between 1000 and 50000 CD8+ cells/well; between 500 and 1000 EBV cells/well; between 1000 and 50000 PBMC/well).

The plates were then incubated overnight (37° C./5% $CO_2$). The next day the plates were washed three times (programme 1, plate type 2, Ultrawash Plus 96-well plate washer, Dynex) with wash buffer and tapped on paper towel to rer11ove excess wash buffer. 100 50 µl primary detection antibody was then added to each well. The primary detection antibody was prepared by adding 550 µl of distilled water to a vial of detection antibody supplied with the Diaclone kit. 100 µl of this solution was then diluted in 10 ml PBS/1% BSA (the volume required for a single plate). Plates were then incubated at room temperature for at least 2 hr prior to being washed three times (programme 1, plate type 2, Ultrawash Plus 96-well plate washer, Dynex) with wash buffer, excess wash buffer was removed by tapping the plate on a paper towel. Secondary detection was performed by adding 100 µl of diluted streptavidin-Alkaline phosphatase to each well and incubating the plate at room temperature for 1 hour. The streptavidin-Alkaline phosphatase was prepared by addition of 10 µl streptavidin-Alkaline phosphatase to 10 ml PBS/1% BSA (the volume required for a single plate). The plates were then washed three times (programme 1, plate type 2, Ultrawash Plus 96-well plate washer, Dynex) with wash buffer and tapped on paper towel to remove excess wash buffer. 100 µl of BCIP/NBT solution, as supplied with the Diaclone kit, was then added to each well. During development plates were covered in foil and left for 5-15 min. Developing plates were regularly checked for spots during this period to determine optimal time to terminate the reaction. The plates were washed in a sink full of tap water to terminate the development reaction, and shaken dry prior to their disassembly into their three constituent parts. The plates were then dried at 50° C. for 1 hr prior to counting the spots that have formed on the membrane using an Immunospot Plate reader (CTL; Cellular Technology Limited).

Results

The anti-CD3 scFv-TCR fusion constructs of FIGS. 4-7 were tested by ELISPOT assay (as described above). The number of ELISPOT spots observed in each well was plotted against the concentration of the test construct using Prism (Graph Pad).

From these dose-response curves, the $EC_{50}$ values were determined ($EC_{50}$ are determined at the concentration of anti-CD3 scFv-TCR fusion that induces 50% of the maximum response).

TABLE 1

| Test Construct | EC50 | EC50 | EC50 |
|---|---|---|---|
| FIG. 7 C-terminal fusion | 5.044e−9 | 1.864e−9 | 2.383e−9 |
| FIG. 5 N-terminal fusion | 8.502e−11 | | |
| FIG. 4 N-terminal fusion | | 4.825e−11 | |
| FIG. 6 N-terminal fusion | | | 3.95e−11 |

These results show that the N-fused constructs of FIGS. 4, 5 and 6 were at least 2 fold more potent in their ability to activate cytotoxic T lymphocytes than the C-fused construct of FIG. 7.

b. Redirection of CD8+ T Cells by the Soluble NY-ESO TCR Fused to an Anti-CD3 Antibody to Kill the IM9 EBV Transformed B Cell Line (Non-Radioactive Cytotoxicity Assay)

The following assay was carried out to demonstrate the activation of cytotoxic T lymphocytes (CTLs) by a TCR-anti-CD3 scFv fusion via specific peptide-MHC complex and the evaluation of the potency of the anti-CD3 scFv portion of the fusion supplied with the CTLs to kill the IM9 cells. This assay is a colorimetric alternative to $^{51}Cr$ release cytotoxicity assays and quantitatively measures lactate dehydrogenase (LDH) which is an enzyme that is released upon cell lysis. Released LDH in culture supernatants is measured with a 30-minute coupled enzymatic assay, which results in the conversion of a tetrazolium salt (INT) into a red formazan product. The amount of colour formed is proportional to the number of lysed cells. The absorbance data is collected using a standard 96-well plate reader at 490 nm.

Materials

CytoTox96® Non-Radioactive Cytotoxicity Assay (Promega) (G1780) contains Substrate Mix, Assay Buffer, Lysis Solution, and Stop Solution Assay media: 10% FCS (heat-inactivated, Gibco, cat#10108-165), 88% RPMI 1640 without phenol red (Invitrogen, cat#32404014), 1% glutamine, 200 mM (Invitrogen, cat#25030024), 1% penicillin/streptomycin (Invitrogen cat#15070063)

Nunc microwell round bottom 96 well tissue culture plate (Nunc, cat#163320)

Nunc-Immuno plates Maxisorb (Nunc, cat#442404)

Method

Target Cell Preparation

The targets cells used in this assay were the IM9 EBV transformed B cell-line derived from a multiple myeloma patient (HLA-A2$^+$ NY-ESO). The Mel526 melanoma cell line was used as a control and is HLA-A2$^+$ NY-ESO. Target cells were prepared in assay medium: target cell concentration was adjusted to $2 \times 10^5$ cells/ml to give $1 \times 10^4$ cells/well in 50 µl.

Effector Cell Preparation

The effector cells used in this assay were CD8$^+$ T cells. The effector to target ratio used was 10:1 ($2 \times 10^6$ cells/ml to give $1 \times 10^5$ cells/well in 50 µl).

Reagent/Test Compound Preparation

Varying concentrations of the NY-ESO TCR-anti-CD3 fusions, having the TCR alpha chain SEQ ID No: 1 and the TCR beta chain-anti-CD3 scFv fusion SEQ ID No: 14, or having the TCR alpha chain SEQ ID No: 1 and the TCR beta chain-anti-CD3 scFv fusion SEQ ID No: 15, were prepared as described in example A1 and prepared for this assay by dilution ($10^{-13}$ to $10^{-8}$M final concentration) into assay media.

Assay Preparation

The constituents of the assay were added to the plate in the following order:

50 µl of target cells, IM9 or Mel526 (prepared as explained previously), to each well 50 µl of reagent (prepared as explained previously) to each well.

50 µl of effector cells (prepared as explained previously) to each well

Several controls were prepared as explained below:

Effector spontaneous release: 50 µl effector cells alone.

Target cells spontaneous release: 50 µl target cells alone.

Target maximum release: 50 µl target cells plus 80 ug/ml digitonin at the start of the assay to lyse cells Assay medium control: 150 µl medium alone.

Experimental wells are prepared in triplicate and control wells in duplicate in a final volume of 150 µl.

The plate was centrifuged at 250×g for 4 minutes then incubated at 37° C. for 24 hours.

The plate was centrifuged at 250×g for 4 minutes. 37.5 µl of the supernatant from each well of the assay plate was transferred to the corresponding well of a flat-bottom 96 well Nunc Maxisorb plate. The Substrate Mix was reconstituted using Assay Buffer (12 ml). 37.5 µl of the reconstituted Substrate Mix was then added to each well of the plate. The plate was covered with aluminum foil and incubated at room temperature for 30 minutes. 37.5 µl of Stop Solution was added to each well the plate to stop the reaction. The absorbance at 490 nm was recorded on an ELIS plate reader within one hour after the addition of Stop Solution.

Calculation of Results

The average of absorbance values of the culture medium background was subtracted from all absorbance values of Experimental, Target Cell Spontaneous Release and Effector Cell Spontaneous Release and Target maximum release.

The corrected values obtained in the first two steps were used in the following formula to compute percent cytotoxicity:

% cytotoxicity=100×(Experimental−Effector Spontaneous−Target Spontaneous)/(Target Maximum Release−Target Spontaneous)

Results

The NY-ESO TCR-anti-CD3 scFv fusion constructs having (i) the TCR alpha chain SEQ ID No: 1 and the TCR beta chain-anti-CD3 scFv fusion SEQ ID No: 14 (C-terminal fusion) or (ii) the TCR alpha chain SEQ ID No: 1 and the TCR beta chain anti-CD3 scFv fusion SEQ ID No: 15 (N-terminal fusion) were tested by LDH release assay (as described above). The % cytotoxicity observed in each well was plotted against the concentration of the test construct using Prism (Graph Pad). From these dose-response curves, the EC50 values were determined (EC50 are determined at the concentration of TCR fusion that induces 50% of the maximum response).

TABLE 2

| Test Construct | EC50 |
| --- | --- |
| C-terminal fusion (SEQ ID No: 1 and SEQ ID No: 14) | $1.2e^{-9}$ |
| N-terminal fusion (SEQ ID No: 1 and SEQ ID No: 15) | $3.2e^{-11}$ |

These results show that the N-terminal fusion comprising the TCR alpha chain SEQ ID No: 1 and the TCR beta chain-anti-CD3 scFv fusion SEQ ID No: 15 was at least 2-fold more potent in its ability to redirect cytotoxic T lymphocytes to kill the target cells than the C-terminal fusion construct comprising the TCR alpha chain SEQ ID No: 1 and the TCR beta chain-anti-CD3 scFv fusion SEQ ID No: 14.

B2. Soluble Chimeric TCR with Cytokines as Effector Polypeptides a. Murine IL-4 Cytokine as Effector Polypeptide The following assay was used to test the biological activity of the cytokine portion of the murine IL-4-TCR fusion constructs of FIGS. 12-13. This is a bioassay using the murine cell line, CTLL-2, which are dependent on murine IL-4 for growth and are used here to demonstrate the biological activity of the cytokine portion of a murine IL-4-TCR fusion.

Materials

CTLL-2 cells, Promega CellTiter-Glo® luminescent cell viability assay (Cat# G7572) including CellTiter-Glo® Buffer and CellTiter-Glo® Substrate (lyophilized) Assay media: RPMI supplemented with 10% heat inactivated foetal bovine serum (Gibco, cat#10108-165), 88% RPMI 1640 (Gibco, cat#42401-018), 1% glutamine (Gibco, cat#25030-024), 1% penicillin/streptomycin (Gibco, cat#15070-063).

CTLL-2 cells were harvested, washed once in assay media (centrifuged at 1200 rpm for 5 mins), counted, and viability was assessed using Trypan blue solution. If viability was less than 80% a ficoll gradient was performed to remove the dead cells (800×g for 15 mins with brake off). Cells were washed a further two times and the volume was adjusted to give 1×10⁵ cells/ml final. CTLL-2 cells were added to a Nunc white flat-bottomed 96-well plate (5000 cells/well), followed by 50 µl titrated concentrations of standard murine IL-4 (Peprotech), or murine IL-4-chimeric TCR fusion constructs of FIGS. 12 and 13 (7 points of 1 in 10 dilutions, from $10^{-8}$ to $10^{14}$M). Controls included cells alone, assay media only, and cells with 200 U/ml Proleukin (Chiron). The plate was incubated at 37° C., 5% CO2 overnight. Following the manufacturers instructions, Cell-Titer-Glo reagent was thawed and added to plate (100 µl per well). The plate was incubated for 10 minutes to stabilise the luminescent signal and then recorded using the luminescence reader. The background signal (cells alone) was subtracted from the readings and a graph plotted in Prism (Graph Pad) so that the EC50's of the murine IL-4-TCR fusion constructs of FIGS. 12 and 13 can be compared with the 'free' recombinant murine IL-4.

Results

TABLE 3

| Test construct | EC50 | EC50 | EC50 |
|---|---|---|---|
| m-IL4 | 4.984e−13 | 3.767e−13 | 5.148e−13 |
| FIG. 13 C-term fusion | 7.464e−12 | | |
| FIG. 12 N-term fusion | | 5.913e−13 | 8.897e−13 |

These results show that the N-fused construct of FIG. 12 was at least 2 fold more potent in its ability to activate cell proliferation than the C-fused construct of FIG. 13.

b. Murine IL-13 Cytokine as Effector Polypeptide

The following assay was used to test the biological activity of the cytokine portion of the murine IL-13-TCR fusion constructs of FIGS. 14-15.

This assay was carried out to demonstrate the activity of the cytokine portion from a cytokine-TCR fusion, i.e. the inhibition of the production of IL-1β by human monocytes. This assay can be used to test cytokine-TCR fusions where the cytokine is murine IL-13.

Materials

Monocytes derived from buffy coats (buffy coats from NBS Bristol Transfusion Service)

Dynal Dynabeads MyPure Monocyte Kit 2 for untouched human cells (113.35) Assay media: 10% foetal bovine serum (heat-inactivated, Gibco, cat#10108-165), 88% RPMI 1640 (Gibco, cat#42401-018), 1% glutamine (Gibco, cat#25030-024), 1% penicillin/streptomycin (Gibco, cat#15070-063)

Wash buffer: 0.01M PBS/0.05% Tween 20 (1 sachet of Phosphate buffered saline with Tween 20, pH7.4 from Sigma, cat# P-3563 dissolved in 1 Litre distilled water gives final composition 0.01M PBS, 0.138M NaCl, 0.0027M KCl, 0.05% Tween 20) PBS (Gibco, cat#10010-015).

HBS⁺S $Ca^{+2}$ and⁺ ⁺² Free (Gibco, cat#1018-165)

Cytokine Eli-pair ELISA kits: IL-1β (Diaclone cat# DC-851.610.020) these kits contain all other reagents required i.e. capture antibody, detection biotinylated antibody, streptavidin-HRP, IL-1β standards, ready-to-use TMB. The following method is based on the instructions supplied with each kit.

Nunc-Immuno plates Maxisorb (Nunc, cat#442404).

Nunc microwell round bottom 96 well tissue culture plate (Nunc, cat#163320)

BSA (Sigma, cat# A3059)

H2SO4 (Sigma cat# S1526)

Trypan blue (Sigma cat# T8154)

Lipopolysaccharides (LPS) derived from *E. coli* 0111:84 (Sigma, cat# L4391)

Recombinant murine IL-13 (Peprotech, cat#210-13) standard used when murine IL-13-TCR fusion reagents tested.

Monocyte Isolation

PBMCs were isolated from buffy coats: a buffy coat was diluted 1 in 2 with HBSS ($Ca^{2+}$ and $Mg^{2+}$ free), diluted blood was layered onto lymphoprep (up to 35 ml blood over 15 ml lymphoprep) and centrifuged 15 min at 800×g (room temp) with the brake off; cells at the interface were removed and washed four times with HBSS and centrifuged at 1200 rpm for 10 min. After the final wash, cells were resuspended 50 ml assay media counted and viability was assessed using Trypan blue solution. Dynal Dynabeads MyPure Monocyte Kit 2 was used to isolate the monocytes. The PBMC were resuspended in PBS/0.1% BSA in 100 µl buffer per 10⁷ cells, 20 µl of Blocking Reagent per 10⁷ cells and 20 µl Antibody Mix per 10⁷ cells were added and cells were incubated for 20 min at 4° C. The cells were washed and resuspended in 0.9 ml PBS/0.1% BSA per 10⁷ cells. Pre-washed beads were added (100 µl per 10⁷ cells), mixed and incubated for a further 15 min at 20° C. with gentle rotation. Rose were resuspended by careful pipetting and 1 ml PBS/0.1% BSA per 10⁷ cells were added. The tube was placed in the Dynal magnet for 2 minutes. Supernatant containing negatively isolated cells was transferred to a fresh tube and counted. Cells were either used immediately or frozen down in 90% FCS/10% DMSO for future use.

Cell Assay Preparation

The ELISA plate was coated with 100 µl/well IL-1β capture antibody in PBS and left at 4° C. overnight. Monocytes were thawed, washed twice in assay media and resuspended at 5×10⁵ cells/ml. The monocytes were plated out into a round bottomed 96 well plate (100 µl per well, i.e. 5×10⁴ per well). LPS, Peprotech recombinant cytokine and test cytokine-TCR fusion proteins were prepared by dilution into assay media to give 4× final concentration. LPS was added in each well (long/ml final) followed by 50 µl of titrated concentrations (6 points of 1 in 10 serial dilutions) of Peprotech recombinant IL-13 ($10^{-8}$ to $10^{-13}$M final) or test cytokine-TCR fusion proteins ($10^{-7}$ to $10^{-13}$M final) in triplicate wells. The plate was incubated at 37° C., 5% CO2 overnight.

IL-1β ELISA

The antibody coated IL-1β ELISA plate was washed three times in wash buffer and blocked with 250 µl PBS/5% BSA/well for at least 2 hours at room temperature (or overnight at 4° C.). The ELISA plate was washed three times in wash buffer and tapped dry. The IL-1β standards were diluted in PBS/1% BSA. The plate containing the cells was centrifuged at 1200 rpm for 5 mins. The supernatant from each well was then transferred to the pre-coated IL-1β ELISA plate. 100 µl of cell supernatant (diluted 1 in 3 with PBS/1% BSA) or standard were added to the relevant wells and 50 µl detection antibody/well (dilution as per kit instructions) were added. The plate was incubated for 2 hours at room temperature. Plates were washed three times in wash buffer. 100 µl of streptavidin-HRP were added per well (dilution as per kit instructions) and plates were incubated at room temp for 20 min. Plates were washed three times in wash buffer. 100 µl of ready-to-use TMB per well were added and plates let to develop for 5-20 min (depending on signal strength) in the dark (under foil). Reaction was stopped by adding 100 µl/well 1M H2 SO4.

Plates absorbance was read on microplate reader at 450 nm and a reference filter set to 650 nm. The amount of inhibition for each titration point is calculated as a percentage of the sample containing monocytes and LPS without cytokine-TCR fusion protein which gives the maximum signal thus producing a dose-response curve.

Results

TABLE 4

| Test construct | EC50 | EC50 |
| --- | --- | --- |
| m-IL13 | 1.535e−10 | 9.534e−11 |
| FIG. 15 C-term fusion | 6.21e−10 | |

TABLE 4-continued

| Test construct | EC50 | EC50 |
| --- | --- | --- |
| FIG. 14 N-term fusion | | 1.493e−10 |

These results show that the N-fused construct of FIG. 14 was at least 2 fold more potent in its ability to inhibit the production of IL-1β by human monocytes than the C-fused construct of FIG. 15.

What is claimed is:

1. A bifunctional molecule, comprising:
a heterodimeric αβ T-Cell Receptor (αβ TCR), wherein the αβ TCR binds specifically to a given pMHC epitope, and
an immune effector polypeptide,
wherein:
the N-terminus of the α chain of the αβ TCR is linked to the C-terminus of a single chain of an immune effector polypeptide comprising CDRs of an anti-CD3 antibody, and
the bifunctional molecule is capable of binding to the given pMHC epitope and CD3, each on a different cell, and thus simultaneously binding to two different cells.

2. A bifunctional molecule, comprising:
a heterodimeric αβ T-Cell Receptor (αβ TCR), wherein the αβ TCR binds specifically to a given pMHC epitope, and
an immune effector polypeptide,
wherein:
the N-terminus of the β chain of the αβ TCR is linked to the C-terminus of a single chain of an immune effector polypeptide comprising CDRs of an anti-CD3 antibody, and
the bifunctional molecule is capable of binding to the given pMHC epitope and CD3, each on a different cell, and thus simultaneously binding to two different cells.

3. The bifunctional molecule of claim 1, wherein the immune effector polypeptide is a single chain immunoglobulin (scFv) which specifically binds to CD3.

4. The bifunctional molecule of claim 2, wherein the immune effector polypeptide is a single chain immunoglobulin (scFv) which specifically binds to CD3.

5. The bifunctional molecule of claim 3, wherein the single chain immunoglobulin comprises SEQ ID NO: 3.

6. The bifunctional molecule of claim 4, wherein the single chain immunoglobulin comprises SEQ ID NO: 3.

* * * * *

SEQUENCE LISTING

<160> NUMBER OF SEQ ID NOS: 16

<210> SEQ ID NO 1
<211> LENGTH: 208
<212> TYPE: PRT
<213> ORGANISM: Artificial Sequence
<220> FEATURE:
<223> OTHER INFORMATION: Description of Artificial Sequence: Synthetic
      T Cell Receptor alpha chain

<400> SEQUENCE: 1

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Thr Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

<210> SEQ ID NO 2
<211> LENGTH: 243
<212> TYPE: PRT
<213> ORGANISM: Artificial Sequence
<220> FEATURE:
<223> OTHER INFORMATION: Description of Artificial Sequence: Synthetic
      T Cell Receptor beta chain

<400> SEQUENCE: 2

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
    50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp

<210> SEQ ID NO 3
<211> LENGTH: 258
<212> TYPE: PRT
<213> ORGANISM: Artificial Sequence
<220> FEATURE:
<223> OTHER INFORMATION: Description of Artificial Sequence: Synthetic
      antibody fragment

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

```
Thr Phe Gly Gln Gly Thr Lys Val Glu Ile Lys Arg Thr Ser Gly Pro
                100                 105                 110

Gly Asp Gly Gly Lys Gly Gly Pro Gly Lys Gly Pro Gly Gly Glu Gly
            115                 120                 125

Thr Lys Gly Thr Gly Pro Gly Gly Glu Val Gln Leu Val Glu Ser Gly
        130                 135                 140

Gly Gly Leu Val Gln Pro Gly Gly Ser Leu Arg Leu Ser Cys Ala Ala
145                 150                 155                 160

Ser Gly Tyr Ser Phe Thr Gly Tyr Thr Met Asn Trp Val Arg Gln Ala
                165                 170                 175

Pro Gly Lys Gly Leu Glu Trp Val Ala Leu Ile Asn Pro Tyr Lys Gly
            180                 185                 190

Val Ser Thr Tyr Asn Gln Lys Phe Lys Asp Arg Phe Thr Ile Ser Val
        195                 200                 205

Asp Lys Ser Lys Asn Thr Ala Tyr Leu Gln Met Asn Ser Leu Arg Ala
    210                 215                 220

Glu Asp Thr Ala Val Tyr Tyr Cys Ala Arg Ser Gly Tyr Tyr Gly Asp
225                 230                 235                 240

Ser Asp Trp Tyr Phe Asp Val Trp Gly Gln Gly Thr Leu Val Thr Val
                245                 250                 255

Ser Ser

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 4

Gly Gly Glu Gly Ser
1               5

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 5

Ala His His Ser Glu Asp Pro Ser Ser Lys Ala Pro Lys Ala Pro
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 6

Gly Gly Glu Gly Gly Gly Ser Glu Gly Gly Gly Ser
1               5                   10

<210> SEQ ID NO 7
<211> LENGTH: 204
<212> TYPE: PRT
<213> ORGANISM: Artificial Sequence
```

<220> FEATURE:
<223> OTHER INFORMATION: Description of Artificial Sequence: Synthetic
      T Cell Receptor alpha chain

<400> SEQUENCE: 7

Ser Gln Leu Ala Glu Glu Asn Pro Trp Ala Leu Ser Val His Glu Gly
1               5                   10                  15

Glu Ser Val Thr Val Asn Cys Ser Tyr Lys Ser Pro Met Ile Asn Leu
            20                  25                  30

Gln Trp Tyr Arg Gln Lys Ser Gly Glu Gly Pro Ala Gln Leu Ile Leu
        35                  40                  45

Ile Arg Ser Asn Glu Arg Glu Lys Arg Asn Gly Arg Leu Arg Ala Thr
50                  55                  60

Leu Asp Thr Ser Ser Gln Ser Ser Ser Leu Ser Ile Thr Ala Thr Arg
65                  70                  75                  80

Ser Glu Asp Thr Ala Val Tyr Phe Cys Ala Thr Asp Pro Leu Gly Tyr
                85                  90                  95

Ile Leu Thr Phe Gly Thr Gly Thr Ser Leu Leu Val Asp Pro Asn Ile
            100                 105                 110

Gln Asn Pro Asp Pro Ala Val Tyr Gln Leu Arg Asp Ser Lys Ser Ser
        115                 120                 125

Asp Lys Ser Val Cys Leu Phe Thr Asp Phe Asp Ser Gln Thr Asn Val
130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser
        195                 200

<210> SEQ ID NO 8
<211> LENGTH: 9
<212> TYPE: PRT
<213> ORGANISM: Mus musculus

<400> SEQUENCE: 8

Leu Tyr Leu Val Cys Gly Glu Arg Gly
1               5

<210> SEQ ID NO 9
<211> LENGTH: 244
<212> TYPE: PRT
<213> ORGANISM: Artificial Sequence
<220> FEATURE:
<223> OTHER INFORMATION: Description of Artificial Sequence: Synthetic
      T Cell Receptor beta chain

<400> SEQUENCE: 9

Gly Gly Ile Ile Thr Gln Thr Pro Lys Phe Leu Ile Gly Gln Glu Gly
1               5                   10                  15

Gln Lys Leu Thr Leu Lys Cys Gln Gln Asn Phe Asn His Asp Thr Met
            20                  25                  30

Tyr Trp Tyr Arg Gln Asp Ser Gly Lys Gly Leu Arg Leu Ile Tyr Tyr
        35                  40                  45

```
Ser Leu Leu Ala Gly His Leu Gln Lys Gly Asp Leu Ser Glu Gly Tyr
     50                  55                  60
Asp Ala Ser Arg Glu Lys Lys Ser Ser Phe Ser Leu Thr Val Thr Ser
 65                  70                  75                  80
Thr Gln Lys Asn Glu Met Ala Val Phe Leu Cys Ala Ser Ser Lys Arg
                 85                  90                  95
Lys Asn Gly Ala Glu Thr Leu Tyr Phe Gly Ser Gly Thr Arg Leu Thr
            100                 105                 110
Val Leu Glu Asp Leu Lys Asn Val Phe Pro Pro Glu Val Ala Val Phe
        115                 120                 125
Glu Pro Ser Glu Ala Glu Ile Ser His Thr Gln Lys Ala Thr Leu Val
130                 135                 140
Cys Leu Ala Thr Gly Phe Tyr Pro Asp His Val Glu Leu Ser Trp Trp
145                 150                 155                 160
Val Asn Gly Lys Glu Val His Ser Gly Val Cys Thr Asp Pro Gln Pro
                165                 170                 175
Leu Lys Glu Gln Pro Ala Leu Asn Asp Ser Arg Tyr Ala Leu Ser Ser
            180                 185                 190
Arg Leu Arg Val Ser Ala Thr Phe Trp Gln Asp Pro Arg Asn His Phe
        195                 200                 205
Arg Cys Gln Val Gln Phe Tyr Gly Leu Ser Glu Asn Asp Glu Trp Thr
    210                 215                 220
Gln Asp Arg Ala Lys Pro Val Thr Gln Ile Val Ser Ala Glu Ala Trp
225                 230                 235                 240
Gly Arg Ala Asp

<210> SEQ ID NO 10
<211> LENGTH: 120
<212> TYPE: PRT
<213> ORGANISM: Mus musculus

<400> SEQUENCE: 10

His Ile His Gly Cys Asp Lys Asn His Leu Arg Glu Ile Ile Gly Ile
 1               5                  10                  15
Leu Asn Glu Val Thr Gly Glu Gly Thr Pro Cys Thr Glu Met Asp Val
            20                  25                  30
Pro Asn Val Leu Thr Ala Thr Lys Asn Thr Thr Glu Ser Glu Leu Val
        35                  40                  45
Cys Arg Ala Ser Lys Val Leu Arg Ile Phe Tyr Leu Lys His Gly Lys
 50                  55                  60
Thr Pro Cys Leu Lys Lys Asn Ser Ser Val Leu Met Glu Leu Gln Arg
 65                  70                  75                  80
Leu Phe Arg Ala Phe Arg Cys Leu Asp Ser Ser Ile Ser Cys Thr Met
                 85                  90                  95
Asn Glu Ser Lys Ser Thr Ser Leu Lys Asp Phe Leu Glu Ser Leu Lys
            100                 105                 110
Ser Ile Met Gln Met Asp Tyr Ser
        115                 120

<210> SEQ ID NO 11
<211> LENGTH: 111
<212> TYPE: PRT
<213> ORGANISM: Mus musculus
```

<400> SEQUENCE: 11

Gly Pro Val Pro Arg Ser Val Ser Leu Pro Leu Thr Leu Lys Glu Leu
1               5                   10                  15

Ile Glu Glu Leu Ser Asn Ile Thr Gln Asp Gln Thr Pro Leu Cys Asn
            20                  25                  30

Gly Ser Met Val Trp Ser Val Asp Leu Ala Ala Gly Phe Cys Val
        35                  40                  45

Ala Leu Asp Ser Leu Thr Asn Ile Ser Asn Cys Asn Ala Ile Tyr Arg
50                  55                  60

Thr Gln Arg Ile Leu His Gly Leu Cys Asn Arg Lys Ala Pro Thr Thr
65                  70                  75                  80

Val Ser Ser Leu Pro Asp Thr Lys Ile Glu Val Ala His Phe Ile Thr
                85                  90                  95

Lys Leu Leu Ser Tyr Thr Lys Gln Leu Phe Arg His Gly Pro Phe
            100                 105                 110

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 12

Gly Gly Glu Gly Gly Gly Pro
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 13

Gly Ser Gly Gly Pro
1               5

<210> SEQ ID NO 14
<211> LENGTH: 501
<212> TYPE: PRT
<213> ORGANISM: Artificial Sequence
<220> FEATURE:
<223> OTHER INFORMATION: Description of Artificial Sequence: Synthetic
      T Cell Receptor beta chain-antibody fusion

<400> SEQUENCE: 14

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
    50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

```
Gly Asn Thr Gly Glu Leu Phe Phe Gly Gly Ser Arg Leu Thr Val
            100                 105                 110

Leu Glu Asp Leu Lys Asn Val Phe Pro Pro Glu Val Ala Val Phe Glu
            115                 120                 125

Pro Ser Glu Ala Glu Ile Ser His Thr Gln Lys Ala Thr Leu Val Cys
            130                 135                 140

Leu Ala Thr Gly Phe Tyr Pro Asp His Val Glu Leu Ser Trp Trp Val
145                     150                 155                 160

Asn Gly Lys Glu Val His Ser Gly Val Cys Thr Asp Pro Gln Pro Leu
                    165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
            195                 200                 205

Cys Gln Val Gln Phe Tyr Gly Leu Ser Glu Asn Asp Glu Trp Thr Gln
            210                 215                 220

Asp Arg Ala Lys Pro Val Thr Gln Ile Val Ser Ala Glu Ala Trp Gly
225                 230                 235                 240

Arg Ala Asp Gly Gly Gly Ser Ala Ile Gln Met Thr Gln Ser Pro
                245                 250                 255

Ser Ser Leu Ser Ala Ser Val Gly Asp Arg Val Thr Ile Thr Cys Arg
            260                 265                 270

Ala Ser Gln Asp Ile Arg Asn Tyr Leu Asn Trp Tyr Gln Lys Pro
            275                 280                 285

Gly Lys Ala Pro Lys Leu Leu Ile Tyr Tyr Thr Ser Arg Leu Glu Ser
            290                 295                 300

Gly Val Pro Ser Arg Phe Ser Gly Ser Gly Ser Gly Thr Asp Tyr Thr
305                 310                 315                 320

Leu Thr Ile Ser Ser Leu Gln Pro Glu Asp Phe Ala Thr Tyr Tyr Cys
                325                 330                 335

Gln Gln Gly Asn Thr Leu Pro Trp Thr Phe Gly Gln Gly Thr Lys Val
            340                 345                 350

Glu Ile Lys Gly Gly Gly Gly Ser Gly Gly Gly Ser Gly Gly Gly
            355                 360                 365

Gly Ser Gly Gly Gly Ser Gly Gly Gly Ser Glu Val Gln Leu Val
            370                 375                 380

Glu Ser Gly Gly Gly Leu Val Gln Pro Gly Gly Ser Leu Arg Leu Ser
385                 390                 395                 400

Cys Ala Ala Ser Gly Tyr Ser Phe Thr Gly Tyr Thr Met Asn Trp Val
                405                 410                 415

Arg Gln Ala Pro Gly Lys Gly Leu Glu Trp Val Ala Leu Ile Asn Pro
            420                 425                 430

Tyr Lys Gly Val Ser Thr Tyr Asn Gln Lys Phe Lys Asp Arg Phe Thr
            435                 440                 445

Ile Ser Val Asp Lys Ser Lys Asn Thr Ala Tyr Leu Gln Met Asn Ser
            450                 455                 460

Leu Arg Ala Glu Asp Thr Ala Val Tyr Tyr Cys Ala Arg Ser Gly Tyr
465                 470                 475                 480

Tyr Gly Asp Ser Asp Trp Tyr Phe Asp Val Trp Gly Gln Gly Thr Leu
                485                 490                 495

Val Thr Val Ser Ser
            500
```

-continued

```
<210> SEQ ID NO 15
<211> LENGTH: 501
<212> TYPE: PRT
<213> ORGANISM: Artificial Sequence
<220> FEATURE:
<223> OTHER INFORMATION: Description of Artificial Sequence: Synthetic
      T Cell Receptor beta chain-antibody fusion

<400> SEQUENCE: 15

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val Gln
130                 135                 140

Pro Gly Gly Ser Leu Arg Leu Ser Cys Ala Ala Ser Gly Tyr Ser Phe
145                 150                 155                 160

Thr Gly Tyr Thr Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
            180                 185                 190

Gln Lys Phe Lys Asp Arg Phe Thr Ile Ser Val Asp Lys Ser Lys Asn
        195                 200                 205

Thr Ala Tyr Leu Gln Met Asn Ser Leu Arg Ala Glu Asp Thr Ala Val
210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
                245                 250                 255

Gly Ser Asn Ala Gly Val Thr Gln Thr Pro Lys Phe Gln Val Leu Lys
            260                 265                 270

Thr Gly Gln Ser Met Thr Leu Gln Cys Ala Gln Asp Met Asn His Glu
        275                 280                 285

Tyr Met Ser Trp Tyr Arg Gln Asp Pro Gly Met Gly Leu Arg Leu Ile
290                 295                 300

His Tyr Ser Val Ala Ile Gln Thr Thr Asp Gln Gly Glu Val Pro Asn
305                 310                 315                 320

Gly Tyr Asn Val Ser Arg Ser Thr Ile Glu Asp Phe Pro Leu Arg Leu
                325                 330                 335

Leu Ser Ala Ala Pro Ser Gln Thr Ser Val Tyr Phe Cys Ala Ser Ser
            340                 345                 350

Tyr Leu Gly Asn Thr Gly Glu Leu Phe Phe Gly Glu Gly Ser Arg Leu
        355                 360                 365
```

```
                                    -continued

Thr Val Leu Glu Asp Leu Lys Asn Val Phe Pro Pro Glu Val Ala Val
        370                 375             380

Phe Glu Pro Ser Glu Ala Glu Ile Ser His Thr Gln Lys Ala Thr Leu
385                 390                 395                 400

Val Cys Leu Ala Thr Gly Phe Tyr Pro Asp His Val Glu Leu Ser Trp
                405                 410                 415

Trp Val Asn Gly Lys Glu Val His Ser Gly Val Cys Thr Asp Pro Gln
                420                 425             430

Pro Leu Lys Glu Gln Pro Ala Leu Asn Asp Ser Arg Tyr Ala Leu Ser
            435                 440                 445

Ser Arg Leu Arg Val Ser Ala Thr Phe Trp Gln Asp Pro Arg Asn His
        450                 455             460

Phe Arg Cys Gln Val Gln Phe Tyr Gly Leu Ser Glu Asn Asp Glu Trp
465                 470                 475                 480

Thr Gln Asp Arg Ala Lys Pro Val Thr Gln Ile Val Ser Ala Glu Ala
                485                 490                 495

Trp Gly Arg Ala Asp
                500

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Leu Leu Met Trp Ile Thr Gln Val
1               5
```